(12) United States Patent
Smith (10) Patent No.: US 10,067,002 B2
(45) Date of Patent: Sep. 4, 2018

(54) RETROFIT GAS KILN ATMOSPHERIC MONITORING SYSTEM

(71) Applicant: Mark Smith, Cornelius, OR (US)

(72) Inventor: Mark Smith, Cornelius, OR (US)

(*) Notice: Subject to any disclaimer, the term of this patent is extended or adjusted under 35 U.S.C. 154(b) by 233 days.

(21) Appl. No.: 15/176,437

(22) Filed: Jun. 8, 2016

(65) Prior Publication Data

US 2017/0356808 A1    Dec. 14, 2017

(51) Int. Cl.
*G01K 7/02* (2006.01)
*G01N 33/00* (2006.01)

(52) U.S. Cl.
CPC ........... *G01K 7/02* (2013.01); *G01N 33/0036* (2013.01)

(58) Field of Classification Search
None
See application file for complete search history.

(56) References Cited

U.S. PATENT DOCUMENTS

| | | | |
|---|---|---|---|
| 6,712,504 B1* | 3/2004 | Dai | G01N 25/56 374/141 |
| 2017/0101964 A1* | 4/2017 | Smiddy | F02M 7/10 |
| 2017/0268462 A1* | 9/2017 | Smiddy | F02M 13/08 |
| 2017/0349866 A1* | 12/2017 | Abbott | C12C 1/13 |
| 2018/0072953 A1* | 3/2018 | Aupperle | F23B 90/08 |
| 2018/0072954 A1* | 3/2018 | Aupperle | F23B 90/08 |

* cited by examiner

*Primary Examiner* — Andre Allen
(74) *Attorney, Agent, or Firm* — Mark S Hubert PC (57) ABSTRACT

An atmospheric monitoring system designed for a low cost retrofit installation into a non commercial potter's gas fired kiln. The system uses a low cost, replaceable, unshielded oxygen sensor incorporated into a modified firebrick for simple installation into a kiln. There is also a high temperature thermocouple inserted through an orifice through the kiln wall such that it senses the temperature adjacent the wares. The system has three embodiments with successive levels of complexity that build onto each other. The simplest system has a base unit for localized visual display of the kiln's atmospheric parameters. The higher levels run a software application on their smart phones that allows for more comprehensive data reporting but more importantly, provide for redundant alarm notification through the LAN and the 4G cell phone network.

14 Claims, 7 Drawing Sheets

RETROFIT GAS KILN ATMOSPHERIC MONITORING SYSTEM

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to gas fired ceramics kilns, and more particularly, to a computerized system for the monitoring of the reduction/oxidation and temperature characteristics of the atmosphere within the kiln.

BACKGROUND

In ceramics, the firing of the glaze or clay body imparts the most notable visual characteristics to the ceramics piece—its color, and luster. These are characteristic of the type of atmosphere that the piece is treated in and the firing recipe used. (The parameters of time, temperature and oxygen levels.)

To make ceramic pieces with the identical visual characteristics requires the piece to undergo the identical atmospheric conditions within the kiln. Unfortunately, the kiln atmospheric conditions vary with current outside atmospheric conditions such as temperature, barometric pressure and dew point. It is also determined by the internal loading and stacking conditions of the objects to be fired. A skilled ceramist must alter the firing parameters of the kiln such as time, temperature and the oxygen-fuel ratio. This is accomplished by adjusting one or more of the following independently or simultaneously—outlet damper, inlet damper, gas pressure, gas flow and gas-oxygen inlet ratio. The problem is that without rapid feedback of the kiln's atmospheric conditions these adjustments are but a crude manner of achieving the proper reducing atmosphere. Often ceramists miss the mark.

Atmosphere monitoring and control devices for high temperature furnaces do exist, but they look at individual parameters, and their costs are prohibitive for the average amateur ceramist. To date there are electronic, computerized atmospheric data reporting systems with specifically designed instrument sensors for gas fired ceramic kilns that look at the requisite ceramic firing parameters and integrate these with the ceramist's recipe. But these are designed into the structure of the kiln by the manufacturer. The various sensors/probes utilized are extremely expensive, proprietary, and fixed in location.

Simply stated, there is no economical solution to date for the ceramist that does not want to spend tens of thousands of dollars. Economical retrofit systems just don't exist.

Thus, an affordable system that allows for the monitoring of the critical gas kiln's atmosphere parameters during the ceramics firing process would provide the ceramist with a plethora of data, allowing them the ability to more precisely and consistently control the firing process. Henceforth, an improved gas kiln atmospheric monitor that would fulfill a long felt need in the ceramics industry. This new invention utilizes and combines known and new technologies in a unique and novel configuration to overcome the aforementioned problems and accomplish this. Such a system is provided by the embodiments set forth below.

BRIEF SUMMARY

In accordance with various embodiments, a kiln atmospheric monitoring system (KAMS) of electronic sensors specifically designed for gas fired kilns, that collates and visually displays real time data of the relevant parameters of interest to a ceramist, is provided.

In one aspect, a computerized kiln atmospheric monitoring system that graphically presents the ceramist with the firing conditions of temperature and oxygen content inside the kiln with respect to time and offers the option to coordinate the firing process with a pre-determined firing schedule.

In another aspect, a kiln monitoring system having dual modes of communication with a cell phone to keep the ceramist informed of his firing process.

In another aspect, an affordable computerized gas kiln atmospheric monitoring system adaptable to be retrofitted onto all sized gas fired kilns is provided.

In yet another aspect, a computerized gas kiln atmospheric monitoring system that prompts the ceramist with suggestions as to how to maintain the kiln atmosphere within input parameters from their firing recipe is provided.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

DETAILED DESCRIPTION OF CERTAIN EMBODIMENTS

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

As used herein the term "transmitter" refers to a piece of electronic equipment capable of both transmitting and receiving electronic signals.

As used herein the term "recipe" refers to a series of parameters for the firing of a ceramic piece that adjust over time to render specific visual aesthetics to the piece. These parameters include but are not limited to temperature, rate of change in temperature, time, and atmospheric oxygen content. A common recipe may include a neutral atmosphere initial temperature ramp, followed by a body reduction, another higher temperature ramp and a final reduction that proceeds over a number of hours and up to a typical temperature target of approximately 2300 degrees F. Herein, a recipe can be kept in a spreadsheet's tabular form that correlates temperature and oxygen content over time. Generally, the recipes include set points for kiln settings for the temperature and oxygen parameters with respect to time of firing.

As used herein the term "data acquisition microcomputer" refers to a general purpose computing device that is capable of performing the algorithmic instructions stored in its non volatile memory. These instructions take real time input digital data and convert it into a format that can be sent to a connected video display device, a connected computer or broadcast to a remote computing device. Higher level instructions allow for the analyses of real time input digital data as it relates to the recipe, allowing for the generation of alerts and indicators of progress for broadcast to the remote computing devices.

In general, embodiments can employ as a processor, any device or combination of devices, that can operate to execute instructions to perform functions as described herein. Merely by way of example, and without limitation, any microprocessor can be used as a processor, including without limitation one or more complex instruction set computing (CISC) microprocessors, such as the single core and multi-core processors available from Intel Corporation™ and others, such as Intel's X86 platform, including, e.g., the Pentium™, Core™, and Xeon™ lines of processors. Additionally and/or alternatively, reduced instruction set computing (RISC) microprocessors, such as the Raspberry Pi™ line of processors, processors employing chip designs by ARM Holdings™, and others can be used in many embodiments. In further embodiments, a processor might be a microcontroller, embedded processor, embedded system, system on a chip (SoC) or the like.

As used herein, the term "processor" can mean a single processor or processor core (of any type) or a plurality of processors or processor cores (again, of any type) operating individually or in concert. The functionality described herein can be allocated among the various processors or processor cores as needed for specific implementations. Thus, it should be noted that, while various examples of processors may be described herein for illustrative purposes, these examples should not be considered limiting.

As used herein the term "USB" may refer to a plug-and-play interface, including USB 3.0 and USB Type-C, for data transfer and electrical power supply between electronic devices, such as computers, media players, keyboards, telephones, digital cameras, scanners, flash drives, joysticks and printers. Generally it supports hot swapping and eliminates the need for many adapters. The physical configuration of the connections may vary slightly and what is referred to as a USB connector may be male or female (plug or socket).

While specific embodiments may describe a USB interface for illustrative purposes, it should be noted that in some embodiments, other interfaces, protocols, connections, and connectors may be substituted, as will be appreciated by those skilled in the art. For example, other interfaces may include, without limitation, Thunderbolt, FireWire, Ethernet, and serial AT attachment (SATA) and eSATA to name but a few alternatives. Thus, these examples should not be considered limiting.

The present invention relates to a novel design for a computerized system of low cost, electronic temperature and oxygen sensors that provide real time atmospheric data for the interior of a ceramics firing kiln to a microprocessor that accumulates, stores, interprets and graphically presents this data with or without reference to a stored/input firing recipe. It is designed so that it can be installed into virtually any gas fired kiln, regardless of the design and age. The kiln atmospheric monitoring system (KAMS) is available in three embodiments, with each successive embodiment built on the framework of the others. The simplest embodiment displays real time data while the more complex embodiments allow for the display of analyzed data and real time data on a networked device, as well as the inputting/editing of firing recipes. The control logic of the algorithmic instructions for all of the various embodiments resides in the base unit of the simplest embodiment. The networked devices of the more complex embodiments utilize downloaded software, but these are used for the display of the real time and analyzed data broadcast from the base system of the simplest embodiment.

Ceramics being fired in a kiln will develop specific colors and luster based on the type of clay body used and the specific glaze in conjunction with the firing recipe used. Generally, a reduction atmosphere is desired wherein a gas kiln is deprived of oxygen, causing incomplete combustion of the fuel and raising the carbon level in the kiln's atmosphere. At high temperatures under a reduction atmosphere, the carbon bonds with and removes the oxygen in the metal oxide glazes which alters the color. (The metals in the glaze are then viewable in an un-oxidized form.) Where there is sufficient iron in the clay body, the reduction will also result in a color change. The time in the firing cycle as well as the temperature when the reduction atmosphere is introduced as well as the duration determines the finished color. The specific look that a glazed or non-glazed piece takes on is set by the ceramist with his own specific recipe.

A conventional gas kiln 2 operates by combusting a gas fuel in a insulated chamber. The fuel to air ratio can be adjusted by manipulation of gas inlet valves, kiln air inlet valve and kiln exhaust dampers. This in turn adjusts the temperature and oxygen content of the inside of the kiln. To create a reduction atmosphere in the gas kiln 2 the oxygen-fuel ratio must be lowered (referred to as a "fuel rich" state.)

The kiln atmosphere monitoring system (KAMS) has three embodiments. The rudimentary system, the cell phone reporting system, (both through the cell phone network and via the internet protocol) and the fully networked system.

Figure 1:
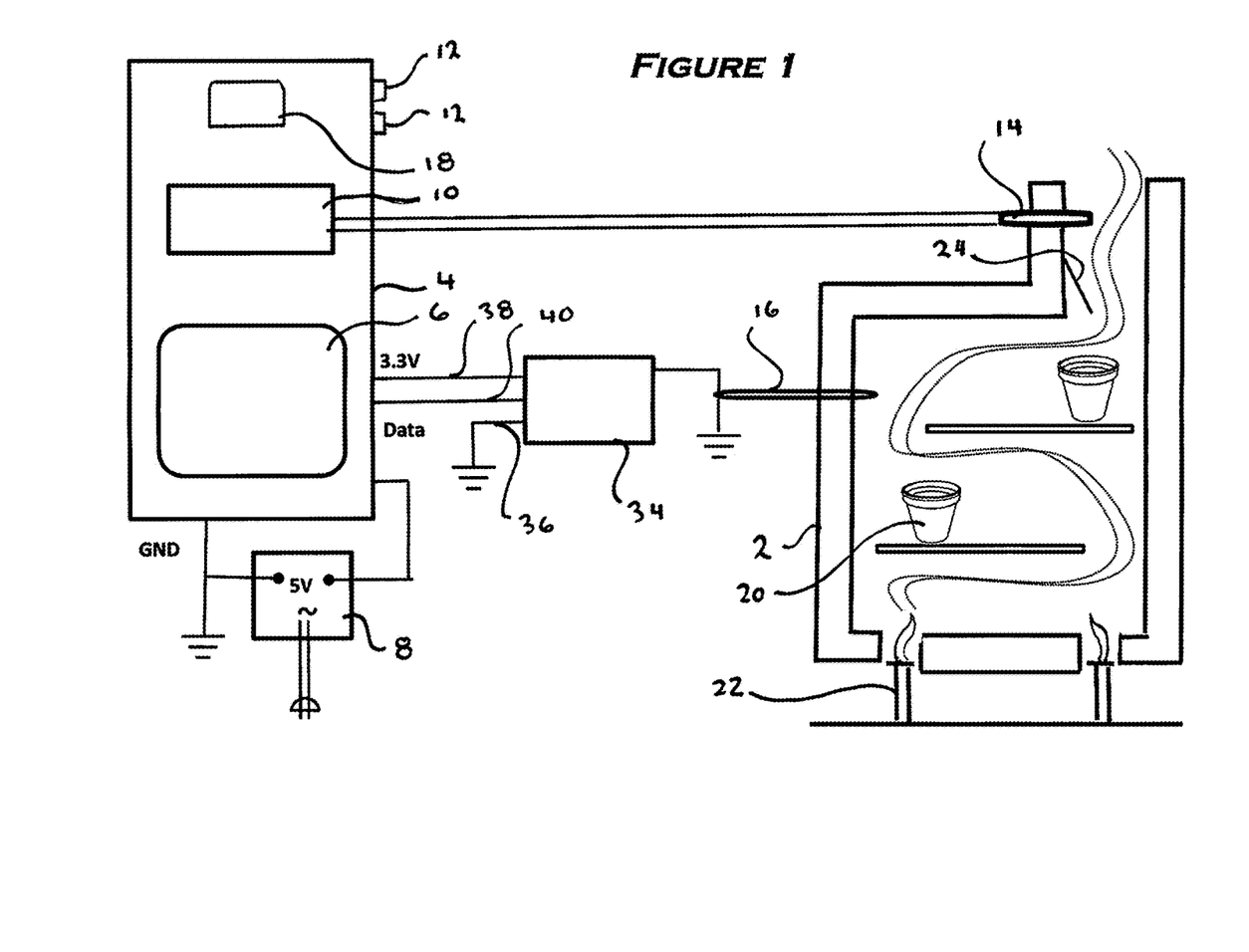
FIG. 1 is a representative view of the simplified embodiment KAMS.

In its simplest embodiment, the rudimentary KAMS reports its real time data to the ceramist on a simple integrated electronic visual display (graphic interface) 6 that shows readings of temperature and oxygen content. This is a self contained base station unit 4 that directly connects to the temperature sensor/s 16 and oxygen sensor/s 14 installed at their specific locations into that particular design of gas kiln. It is designed for mounting in a visible location about the kiln 2. This base station 6 is a housing that integrates a power supply 8, a data acquisition microprocessor 18, a graphic interface 6, an analog to digital converter 10, and a set of operatively connected ports 12 for connection of the two sensors 14 and 16, any external memory and a wireless Ethernet adaptor. (FIG. 1)

The heart of the system is the novel probes/sensors used for the temperature and oxygen monitoring and the dual modes of alarm communication.

The simplest embodiment uses but one temperature sensor 16 which would be mounted preferably at a location inside the kiln 2 that is representative of the temperature that the wares 20 experience when being fired. It must not be located too close to the gas burners 22. The physical structure of the specific kiln will often determine where the practical location for this sensor is since its installation requires drilling into the kiln brick. Where the temperature sensor exits the kiln there will be a mechanical sealing of the void around the temperature sensor 16. Generally this will be accomplished by the packing of a high temperature insulating material.

The first, simplest embodiment is designed for use with K or R type thermocouple. The type K thermocouple is preferred because of its low cost. This thermocouple uses chromel—alumel composition having a sensitivity of approximately 41 μV/° C., is inexpensive and operates in a −200° C. to +1350° C. range (−330° F. to +2460° F.). The type K thermocouple however, does not last long in a reducing atmosphere as the chromium in the chromel alloy oxidizes. This wear is expected and temperature sensor replacement will be required after multiple firings. The temperature sensor 16 is located in the body of the kiln 2 in proximity to the wares 20. The simplest embodiment uses but one oxygen sensor 14 optionally placed inside the kiln but in the exhaust gas stream downstream of the exhaust damper 24.

Figure 3:
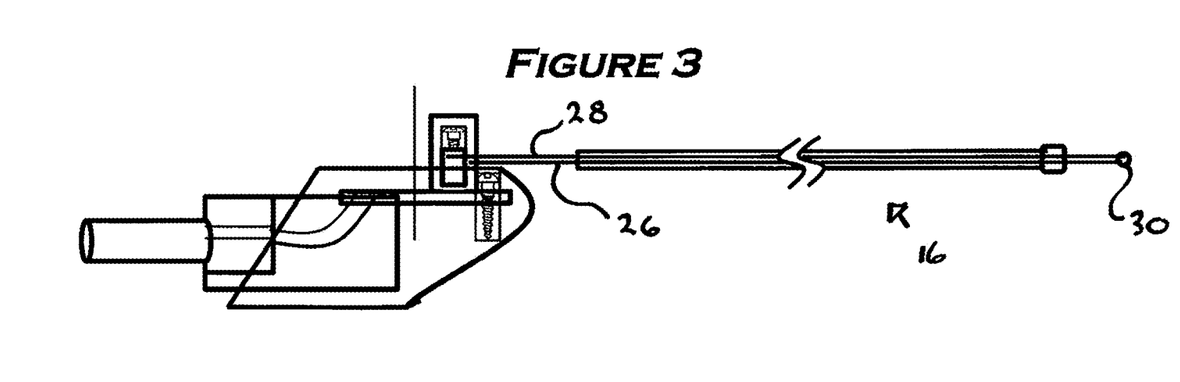
FIG. 3 is a top view of the temperature sensor.
Figure 4:
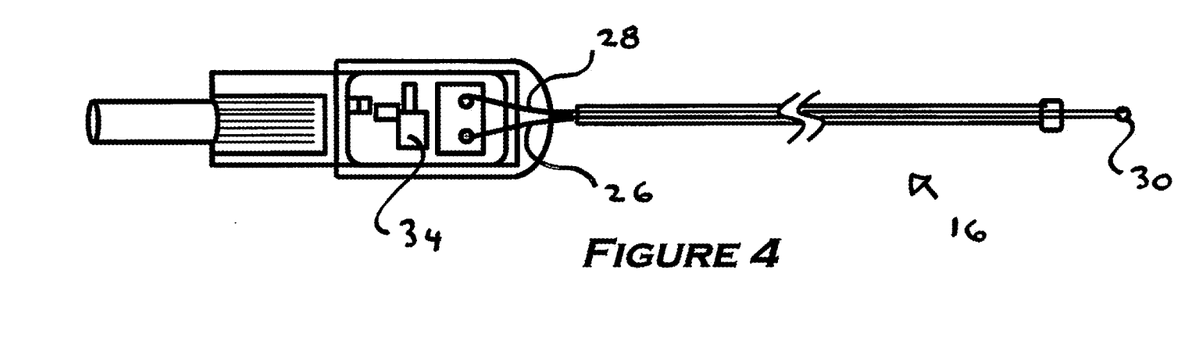
FIG. 4 is a side view of the temperature sensor.
Figure 7:
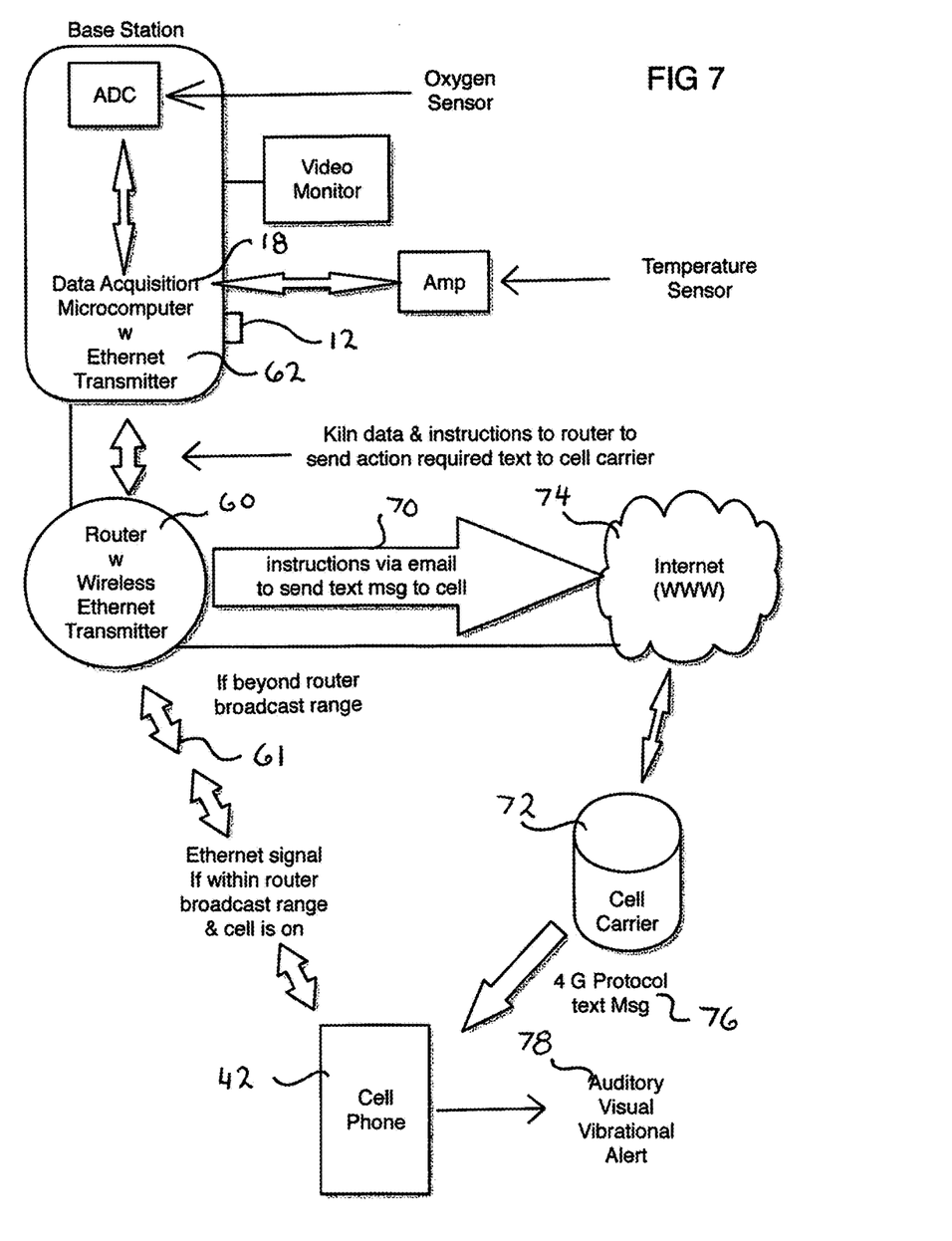
FIG. 7 is a diagrammatic representation of the cell phone reporting KAMS embodiment.
Figure 8:
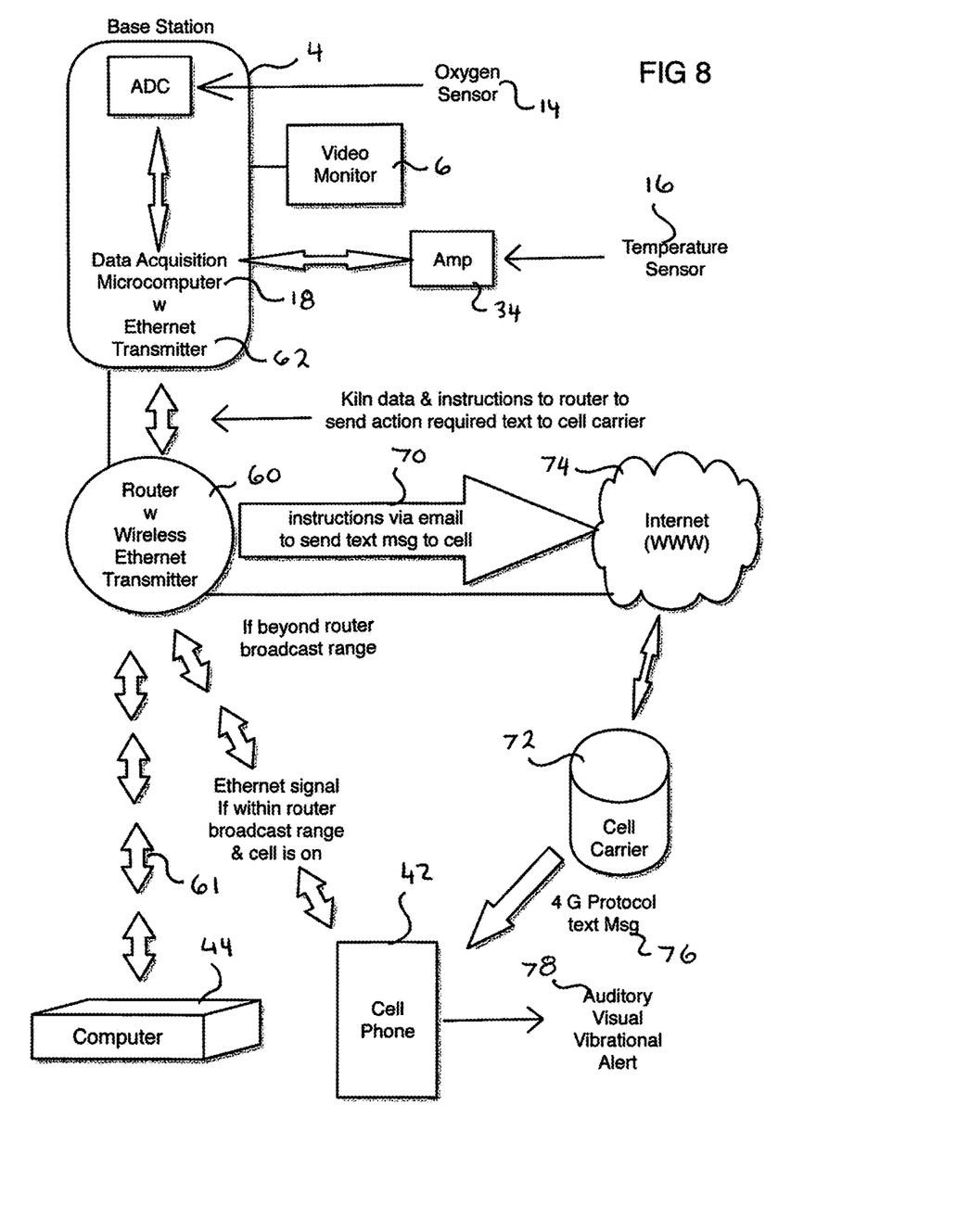
FIG. 8 is a diagrammatic representation of the fully networked KAMS embodiment.

Looking at FIGS. 3 and 4 it can be seen that the chromel wire 26 and the alumel wire 28 are held in a spaced, separated configuration except for their junction 30 at the distil end tip (downstream of a ceramic spacer 32). The wires are insulated by a ceramic braid along their length to prevent both short circuiting and oxidation. Only the braided portion will extend beyond the interior edge of the orifice formed through the kiln's firebrick. The sensor should be extended as far into the kiln as possible without contacting any objects. The proximal ends of the separated wires are operationally connected to a cold junction compensated thermocouple amplifier 34. The amplifier amplifies the electrical signal, and converts the input data to output digital format. There are three conductor wires connected between the amplifier and the data acquisition microcomputer 18. One wire is ground 36, one wire transfers the data signal 40 to the microcomputer and one dedicated wire 38 supplies the operating power to the amplifier. The preferred embodiment uses a 3.3 V system for both data and power. The data acquisition microcomputer 18 polls the thermocouple amplifier 34 and obtains the digital signal (serial data in the form of one's and zeros). The set of algorithmic instructions input and stored on the data acquisition computer 18 converts this serial data into a format (specific to the chosen data acquisition microcomputer), that can be sent to the base station's integrated, connected graphic interface 6 (to visually indicate the temperature in numerical format), a cell phone 42, or a connected computing device 44 (for higher level analysis, display and coordination of the firing process), or broadcast to a remote computing device. (FIGS. 7 and 8)

The temperature sensor 16 is inserted via an orifice drilled into the fire bricks of the kiln 2. The orifice is drilled at the most practical location for monitoring the average temperature seen by the wares when firing. After insertion of the temperature sensor to the desired length, the orifice is sealed with an insulating material such as high temperature fiber. It is a low cost, replaceable thermocouple.

The first, simplest embodiment also uses but one oxygen sensor 14. (FIG. 2) The preferred location for the oxygen sensor 14 is in the lowest practical position in exhaust gas flue before the exhaust damper. 24 (Although in certain kilns 2 placement of the oxygen sensor 14 may be more practical after the exhaust damper 24.) The installation of the oxygen sensor 14 is a more complicated process than for the temperature sensor 16 as it requires the removal of a firebrick from the flue which will be replaced by the entire oxygen sensor body 16.

Figure 2:
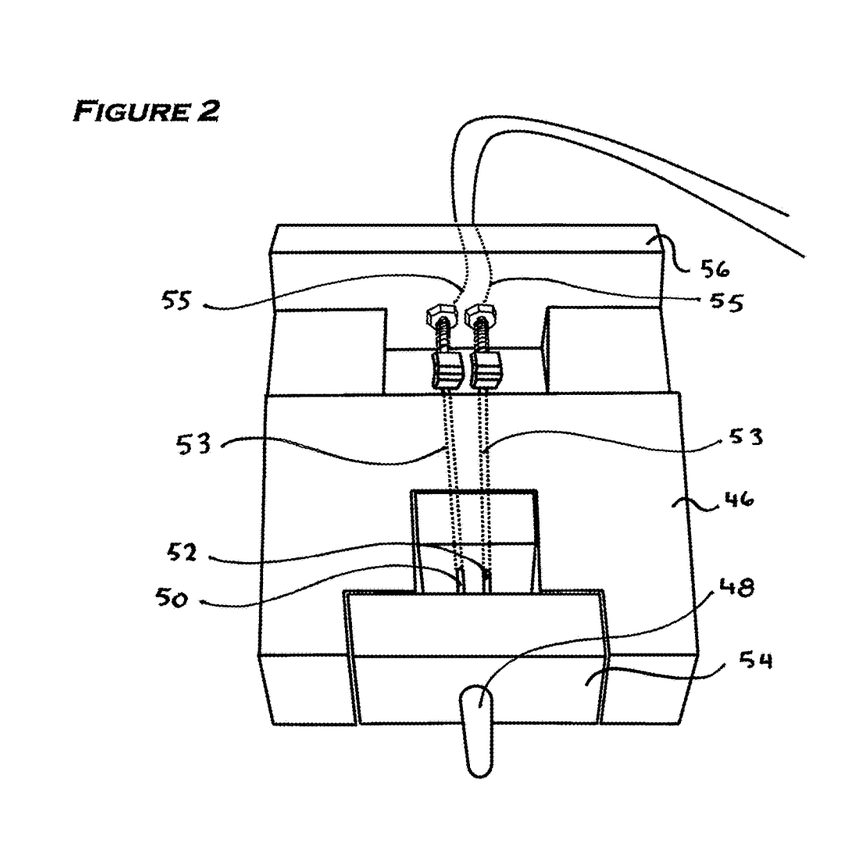
FIG. 2 is a top perspective view of an embodiment of the oxygen sensor.

The oxygen sensor 14 is a hollow frustoconical tip 48 coated with platinum on both the inside surface and the outside surface. This tip is unshielded and its outer platinum surface is in direct contact with the kiln's atmosphere. There is an open channel in the body of the sensor that allows outside air to migrate into the inner cavity of the tip. After approximately 1400 degrees F., when free oxygen molecules strike the zirconium, an electric potential is produced at the platinum's surface. There are two electrodes, one electrode connected to the outside face 50 and one electrode to the inside face 52 of the tip. Since there is more oxygen in the interior than the exterior face when there is a reducing atmosphere in the kiln, an electric potential between the two electrodes is generated such that a low voltage analog signal is produced. This low voltage analog signal is feed to an analog to digital converter 10 that stores the data in its volatile storage register. The data acquisition microcomputer 18 polls the analog to digital convertor 10 and obtains the digital signal (serial data in the form of ones and zeros). A second set of algorithmic instructions (specific to the chosen data acquisition microcomputer), input and stored on the data acquisition microcomputer 18, converts this serial data into a format that can be sent to the base station's integrated connected graphic interface 6 (to visually indicate the free oxygen in numerical format with respect to the ambient air in an arbitrary scale with the lowest range indicating oxidizing atmospheres and the higher range indicating reduction atmospheres), a connected computing device 44 (for higher level analysis, display and coordination of the firing process), or broadcast to a cell phone 42 or a remote computing device.

The oxygen sensor body 46 is made of a fire brick with enough material removed to accommodate a ceramic face plate 54 on its front side from which the platinum frustconical tip 48 of the oxygen sensor 14 is secured and extends normally therefrom. The sensor electrodes 50 and 52 extend from the back of the tip and pass through a pair of parallel channels 53 cut in the fire brick adjacent and behind the rear of the face plate 54. There is a ceramic backing plate 56 affixed to the rear of the fire brick that has a second set of orifices 55 through which the electrodes each pass. On the two electrodes 50 and 52, in the space between the channels cut in the fire brick and the backing plate 56 is a pair of compression springs 58 secured between the backing plate 56 and the electrodes 50 and 52, so as to maintain a forward pressure on the electrodes from the backing plate. This serves to secure both the electrical connection and the electrodes on the oxygen sensor body. This compensates for the changes in length due to thermal expansion. The entire oxygen sensor body 46 is sized for transposition with a kiln brick. Insertion location is adjacent to the exhaust damper 24. (This is preferably downstream of the exhaust damper 24 however in different kilns, it may be located upstream of the damper 24.)

It is to be noted that while the simplest embodiment uses but one temperature sensor 16 and one oxygen sensor 14, other embodiments as discussed herein, may utilize multiple sensors, although for the purpose of description herein all embodiments will be discussed with but a single pair of sensors. These would be placed around the kiln 2 in practical, strategic areas for the monitoring of the temperature and oxygen parameters with respect to the location of the initial sensors. These additional data streams may be used to further represent the atmospheric conditions in the kiln 2 and may be averaged and analyzed with the initial data streams.

In its second embodiment, (FIG. 7) the cell phone reporting system, the rudimentary KAMS is identical to the first base station embodiment but has additional hardware and software operationally coupled to the data acquisition microcomputer 18. This embodiment has more functionality than the simplest embodiment, and reports its real time and analyzed data to the ceramist via their cell phones 42. However, since it is an extension of the first embodiment, in the event of a power failure or connectivity loss in the cell phone, there is redundancy with the base station 4. Additionally this second embodiment has a dual alarm reporting system.

The cell phone reporting KAMS adds four elements/ components to the data acquisition microcomputer 18, as well as another algorithmic set of instructions. First, it adds a wired or wireless Ethernet transmitter 62 (preferably via a USB connection.) This operationally connects the base station 4 to the user's IP router 60, which then enables the wireless transmission 61 of the serial data from the base station 4, via internet protocol on the LAN, to all the connected devices on that router's network including the user's cell/smart phone 42. (However this transmission of serial data to the cell phone 42 is only received by the cell phone 42 when the cell phone is turned on and within range of the wireless router 60.)

Figure 6:
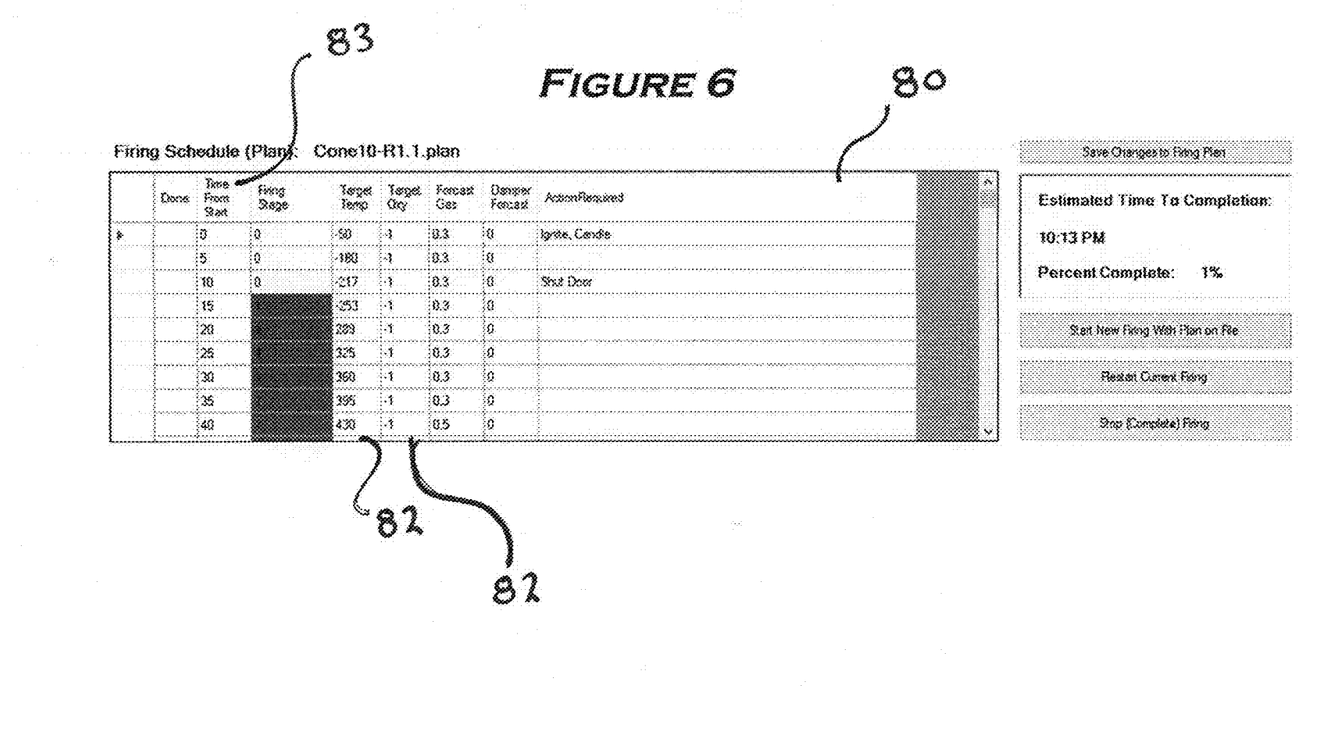
FIG. 6 is a screen capture of a KAMS recipe in use by the system.

Second, it adds recipe software with algorithmic instructions and data that are downloaded into the microcomputer 18. (These are downloaded into the microcomputer 18 via a non volatile memory device such as an SD card or thumb drive inserted into an operationally mating connective port 12 on the base station 4.) This software provides instructions for coordinating the firing process. The recipe (FIG. 6) has target or set points 82 with respect to the temperature and oxygen content for given times. The recipe software enables the microcomputer to compare the set points of the recipe with the real time data. This then generates the alerts. The set of instruction algorithms that are added, tell the data acquisition computer 18 to signal the router 60 instructing it to send an email message 70 via the LAN (in SMTP format) to the cell phone carrier 72 via the internet 74 (world wide web.) This email message 70 provides instructions to the cell phone carrier 72 to convert or translate the email message 70 into a text message 76 and send it to the cell phone via the cell carrier's network protocol (often referred to as 4G telecommunications technology network.) This utilizes the phone's existing text message application to provide the alert 78 as a text message that appears on the ceramist's cell phone 42 as an alert and instructs the ceramist when to take action.

Third, it adds a cell phone 42 and lastly, a software application that is downloaded and run on the cell phone 42. This software application allows the ceramist to view real time kiln temperature and oxygen content data, with respect to the recipe's set points 82 and parameters so as to allow them to monitor the firing progress via their cell phone display.

The base station 4 has dual communication modes with the cell phone 42 and at all times communicates with the cell phone 42 in two different ways. It communicates its serial data over the LAN, however critical messages (determined by the data acquisition microcomputer's comparisons between the real time data of the kiln atmosphere and the recipe set points/parameters 82) are sent via email 70. This dual communication system exists because the alert 78 may be generated when the ceramist is not running the cell phone application, is out of router range, the ceramist is offline, or the cell phone turned off. It is necessary that critical alerts 78 reach the ceramist.

There is the need for text messaging alerts 78 because the firing process is lengthy, generally taking from seven to ten hours. The ceramist is unlikely to have the application open on their phones 42 this entire time. Should a parameter of temperature, time or oxygen level fall outside the set recipe parameters 82 and need adjustment/attention, the ceramist would be able to be notified.

The second embodiment adds a level of complexity and data reporting well beyond that displayed by the base model. This will incorporate real time temperature and oxygen level reporting as well as data analyzed by the microcomputer 18. These are represented on the graphic interface of the phone 42 via the format established by an application downloaded into the phone's operating system.

The software application downloaded onto the data acquisition microcomputer 18 provides a flexible firing recipe in a tabular format 80 (edited via a connected computing device) into which the real time data is processed. (FIG. 6) The tabular format 80 has temperature and oxygen level set points 82 inserted at various times 83 in the table. The software application also has set of algorithms to compare the real time data to the recipe set-points 82 and generate alert notifications as appropriate. It produces a set of trending forecasters for the parameters of the kiln's atmosphere. This set of KAMS data is broadcast as discussed above. Finally, the software application download has a listening feature that allows it to be discovered by any other LAN networked device that is running the KAMS software application. Once discovered, the data from the data acquisition microcomputer 18 can be pushed to the other LAN networked devices.

The data acquisition microcomputer 18 can be discovered and put into operational communication with any device on the LAN that is running the KAMS software application designed for communication with the base station 4.

The KAMS software application is downloaded into the phone's operating system. It does not provide logic instruction for the processing or analysis of the real time data generated by the two sensors 14 and 16. (This is done by the microcomputer 18.) Rather, it does two things. It has a discovery mechanism, that once the phone 42 is connected to the LAN (and it is prompted to do so) it will find any KAMS base station 42 connected to the same LAN. Thereafter, communication between these two LAN connected devices will be established following internet protocol, as is well known in the industry. Secondly, it provides an aesthetic viewable format so the graphic interface of the phone 42 can display the KAMS data.

Figure 5:
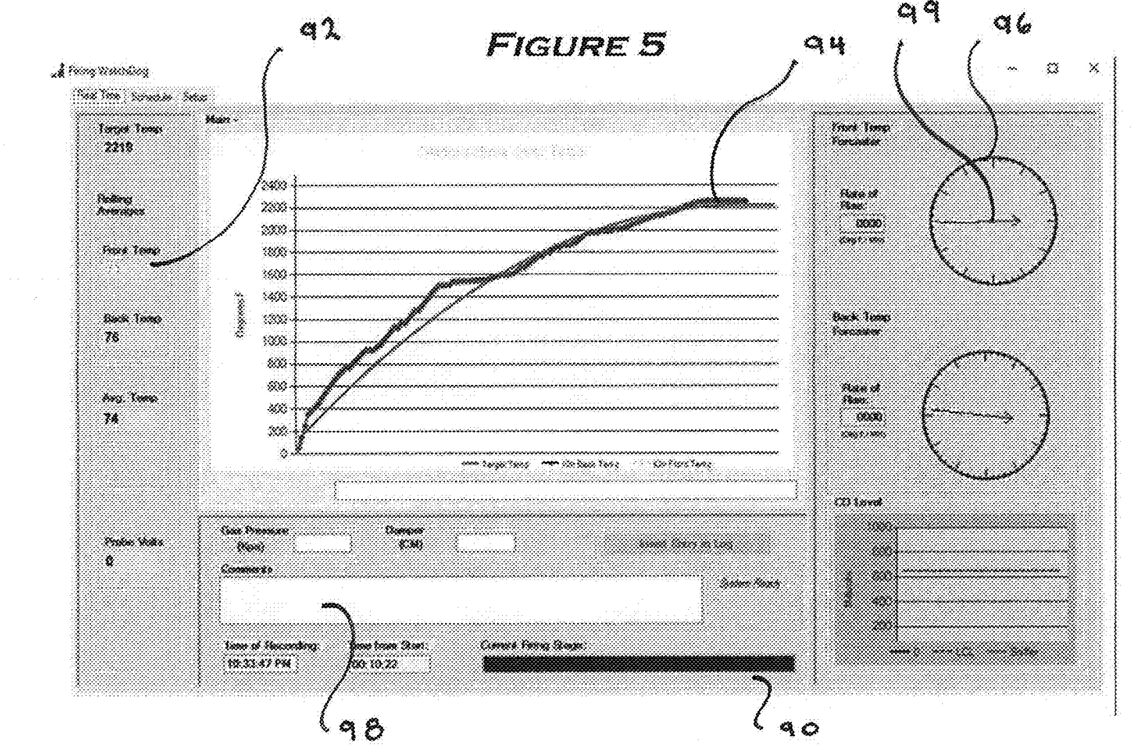
FIG. 5 is a screen shot of the main software application interface.

Looking at FIG. 5 a screen shot of the graphic interface 90 for the cell phone and the networked computer 44 can be seen. This displays the real time data and the data analyzed by the algorithms in the data acquisition microcomputer 18. This data includes but is not limited to: target temperature, temperature from the various probes about the kiln, the oxygen content (as CO level), temperature forecasters (indicating the momentary rate of rise or fall of temperature), the time temperature graph, the firing state, time, elapsed time, and alert notifications. Optionally, the damper position and gas settings may be provided if the ceramist wishes to incorporate additional position sensors into his kiln.

It is to be noted that the trending indicators 96 are displayed in a compass format wherein there are as directional arrows 99 that indicate a rise or fall of temperature. This forecast is calculated by performing a linear regression on the last series of temperature data points. This provides the ceramist with an instantaneous response to actions taken with respect to gas and damper settings. Without this information, the ceramist must wait until there is a significant trend in the kiln temperatures. This is a slow process taking about 15-30 minutes. Unfortunately, this time lag then results in gross temperature swings, longer firing and wasted fuel. All contributing problems with the appearance of the wares after the firing process.

The alerts 78 are textual notifications of various actions required or deviations in the kiln atmosphere with respect to the recipe as generated by the data acquisition microcomputer 18. A non-exhaustive list of these alerts are: low temperature, high temperature, improper reducing environment, close damper, open damper, increase gas, decrease gas, shut down kiln, and observe pyrometric cones.

The third embodiment is a fully networked KAMS. (FIG. 8) This adds a computer 44 wirelessly, as another networked device, (in addition to the smart cell phone 42) to the base unit 4. This is accomplished in the same manner as discussed above with the cell phone 42 once the KAMS software application is downloaded onto the computer 44 and the computer 44 is connected to the same LAN as the base station 4. The display of the graphic interface is identical to or mimics that of the cell phone. With connection between the data acquisition microcomputer 18 and the LAN connected computer 44, recipe management can be performed on a robust keyboard and UI. Recipe management is accomplished by changing the set points 82 in the table of the firing recipe.

In the preferred embodiment KAMS utilizes a computer 44 that presents much more sophisticated real time and trending data, as well as optionally allowing the ceramist to input their own recipe. The kiln's gas flow and dampers can then be adjusted to maintain the temperature and oxygen targets during the firing period as specified by the recipe, as both these parameters are displayed in real time in comparison with the recipe.

As can be seen from the above disclosure, a gas kiln atmospheric monitoring system (KAMS) that provides a dual mode of alarm notification has been disclosed such that one skilled in the art would be able to both make and use it. The operational process or methodology of its first, second and third embodiments, the base station, the cell phone alarming KAMS and the fully networked KAMS, encompasses the following sequential steps:

For the first embodiment, a method of providing a ceramist with visual data about the temperature and oxygen content of the atmosphere of their gas kiln during the firing process of wares comprises the following steps:

Producing a voltage relative to the kiln's internal temperature by a thermocouple imbedded into the gas kiln;

Receiving a voltage signal from the thermocouple at the thermocouple amplifier;

Producing a binary data value in the register of the thermocouple amplifier that is a digital representation of the kiln's internal temperature;

Producing a voltage relative to the free oxygen level of the Kiln's internal atmospheric from an oxygen sensor embedded in the kiln;

Producing a binary data value in the register of an analog to digital converter connected to the oxygen sensor representative of the kiln's internal atmosphere;

Reading of the binary data values of the kiln's internal temperature stored in the thermocouple amplifier register following non-volatile instructions in the base station microcomputer and displaying the kiln's internal temperature to the user via the base station monitor; and Reading of the binary data values of the kiln's internal oxygen level stored in the analog to digital convertor thermocouple amplifier register following on-volatile instructions in the base station microcomputer and displaying the kiln's internal oxygen level to the user via the base station monitor.

For the second embodiment, a method of providing a ceramist with visual data about the temperature and oxygen content of the atmosphere of their gas kiln during the firing process of wares, as well as alert messages presented in dual formats, comprises the following steps:

Storage of firing recipe data in the persist-able memory of the base station microcomputer;

Connecting the base station's microcomputer to a local area network;

Installing a KAMS software application for the receipt and display of real time temperature and atmospheric conditions as well as correlated data onto user's mobile device and operationally connecting the mobile device to the same local area network the base station is connected to;

Producing a voltage relative to the kiln's internal temperature by a thermocouple imbedded into the gas kiln;

Receiving a voltage signal from the thermocouple at the thermocouple amplifier;

Producing a binary data value in the register of the thermocouple amplifier that is a digital representation of the kiln's internal temperature;

Producing a voltage relative to the free oxygen level of the Kiln's internal atmospheric from an oxygen sensor embedded in the kiln;

Producing a binary data value in the register of an analog to digital converter connected to the oxygen sensor representative of the kiln's internal atmosphere;

Reading of the binary data values of the kiln's internal temperature stored in the thermocouple amplifier register following the non-volatile instructions in the base station microcomputer and displaying it to the user via the base station monitor;

Reading of the binary data values of the kiln's internal oxygen level stored in the analog to digital convertor thermocouple amplifier register following the non-volatile instructions in the base station microcomputer and displaying it to the user on the base station monitor;

Correlating current temperature and atmospheric conditions in the kiln to set-points in the recipe for the given elapsed time in the firing process according to the non-volatile instructions input into the base station microcomputer;

Generating correlated data including real time time/temperature charts, temperature rise/fall indicators, oxygen content charts, firing progress tables and alerts according to the non-volatile instructions input into the base station microcomputer;

Sending an electronic message to the user's mobile device carrier via the local area network, directing the mobile device carrier to send an alert text message to the user's mobile device via the mobile device's carrier system when an alert is generated;

Sending real time temperature and atmospheric conditions as well as correlated data to the user's mobile device via a local area network;

Displaying real time temperature and atmospheric conditions and correlated data on the user's mobile device; and Accumulating a summary of the firing data in the persistable memory of the base station's microcomputer for later review.

For the third embodiment, a method of providing a ceramist with visual data about the temperature and oxygen content of the atmosphere of their gas kiln during the firing process of wares, as well as alert messages presented in dual formats, is identical to the methodology steps of the second embodiment except it comprises the following additional steps:

Installing a KAMS software application onto user's personal computer and operationally connecting the personal computer to the same local area network the base station is connected to;

Sending real time temperature and atmospheric conditions as well as correlated data from the base station to the user's personal computer via a local area network;

Optionally, selecting a recipe or transferring a recipe from the base station's microcomputer to the user's personal computer;

Altering the parameters in the recipe on the user's personal computer;

Transferring the altered recipe on the user's personal microcomputer to the base station microcomputer for subsequent use;

Optionally, selecting a recorded firing result from the base station microcomputer's non-volatile memory and reviewing it on the user's personal computer for comparison of recipe set points with actual temperature and oxygen content results.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture, but instead can be implemented on any suitable hardware, firmware, and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added, and/or subtracted from among other described embodiments, unless the context dictates otherwise. Consequently, although several exemplary embodiments are described above, it will be appreciated that the invention is intended to cover all modifications and equivalents within the scope of the following claims.

Having thus described the invention, what is claimed as new and desired to be secured by Letters Patent is as follows:

1. An atmospheric monitoring system comprising;
   a base station, said base station having a power supply, a graphic interface, a data acquisition microcomputer, an analog to digital convertor and a series of connection ports all operatively connected within a base station housing;
   an oxygen sensor operatively connected to said analog to digital convertor in said base station through one of said connection ports for the transmission of real time oxygen content serial data;
   a temperature sensor operatively connected to said base station through one of said connection ports for the transmission of real time temperature serial data; and
   wherein said base station's graphic interface displays real time serial temperature and oxygen data obtained from said sensors; and
   wherein said oxygen sensor has a sensor body formed from a fire brick and dimensionally sized for transposition with a removed kiln fire brick.

2. The atmospheric monitoring system of claim 1 wherein said sensor has a sensor body with a ceramic face plate thereon its front side from which a hollow, platinum frustoconical tip extends, said tip having two electrodes connected thereto and passing through a pair of channels cut in said body and a rear backing plate, wherein said electrodes are connected to a set of springs to maintain a forward pressure on said electrodes from said backing plate.

3. The atmospheric monitoring system of claim 1 wherein said oxygen sensor is placed into a gas fired kiln upstream of a flue damper.

4. The atmospheric monitoring system of claim 3 wherein said temperature sensor is a K type thermocouple operatively connected sequentially to an amplifier then to said base station.

5. An atmospheric monitoring system comprising;
a base station, said base station having a power supply, a graphic interface, a data acquisition microcomputer, an analog to digital convertor and a series of connection ports all operatively connected within a base station housing;
an oxygen sensor operatively connected to said analog to digital convertor in said base station through one of said connection ports for the transmission of real time oxygen content serial data;
a temperature sensor operatively connected to said base station through one of said connection ports for the transmission of real time temperature serial data; and
a first set of set of algorithmic instructions stored in said data acquisition microcomputer, said algorithmic instructions enabling said microcomputer to convert said serial data into a format specific to said data acquisition microcomputer that is transferred to said graphic interface to visually display temperature serial data and oxygen content serial data in a numeric format; and
wherein said base station's graphic interface displays real time serial temperature and oxygen data obtained from said sensors; and
wherein said base station further comprises a second set of algorithmic instructions loaded into said microcomputer, an Ethernet transmitter operatively connected to said microcomputer and a local IP router, and recipe software with a third set of algorithmic instructions loaded into said microcomputer; and
wherein said second set of algorithmic instructions directs said microcomputer to perform analysis of said serial data and to transmit said serial data via said IP router wirelessly to connected devices on said router's network; and
wherein said third set of algorithmic instructions enables said microcomputer to generate alerts based on comparisons of a series of set points of said recipe to said real time serial temperature and oxygen data, and to send said alerts to said router for broadcast to connected devices on a local area network of said router.

6. The atmospheric monitoring system of claim 5 wherein said microprocessor sends dual alerts via said router.

7. The atmospheric monitoring system of claim 6 wherein said microprocessor sends a first alert via said router for broadcast to connected devices on said router's local area network, and sends a second alert to said router with instruction to said router to generate an email message vial said local area network to a cell phone carrier with further instructions for the cell phone carrier to convert said email message to a text message and to send it to a cell phone as a text message alert.

8. The atmospheric monitoring system of claim 7 further comprising a software application that is downloaded onto connected devices on a local area network of said router, said application provides a format for the visual presentation of said real time serial data and said analyzed data on a graphic interface of said connected devices.

9. The atmospheric monitoring system of claim 8 wherein said cell phone is a device connected to said router's local area network.

10. The atmospheric monitoring system of claim 9 wherein a computer is a device connected to said router's local area network.

11. The atmospheric monitoring system of claim 8 wherein said format for visual representation includes real time serial data generated by the microcomputer about temperature and oxygen content as well as serial data analyzed by said microcomputer content application.

12. The atmospheric monitoring system of claim 11 wherein said serial data analyzed includes at least one trending indicator of temperature calculated by performing a linear regression on the temperature data, said trending indicator visually represented in a compass format with directional arrows indicating a rise or fall in temperature.

13. The atmospheric monitoring system of claim 11 wherein said serial data analyzed includes a time temperature graph.

14. A method of providing a ceramist with visual data about the temperature and oxygen content of the atmosphere of a gas, as well as alert messages presented in dual formats, comprising the following steps:
storing firing recipe data in a persist-able memory of a base station microcomputer;
connecting said base station's microcomputer to a local area network;
installing a software application for the receipt and display of real time temperature and atmospheric conditions as well as correlated data onto a user's mobile device and operationally connecting said mobile device to said local area network;
producing a voltage relative to said gas kiln's internal temperature by a thermocouple imbedded into said gas kiln;
receiving a voltage signal from said thermocouple at a thermocouple amplifier;
producing a binary data value in a register of said thermocouple amplifier that is a digital representation of said gas kiln's internal temperature;
producing a voltage relative to a free oxygen level of said gas kiln's internal atmosphere from an oxygen sensor embedded in said gas kiln;
producing a binary data value in a register of an analog to digital converter connected to said oxygen sensor that is representative of said gas kiln's internal atmosphere;
reading of said binary data values of said gas kiln's internal temperature stored in said thermocouple amplifier register following a set of non-volatile instructions in said base station microcomputer and displaying it to said user via said base station monitor;
reading of binary data values of said gas kiln's internal oxygen level stored in said analog to digital convertor thermocouple amplifier register following said non-volatile instructions in said base station microcomputer and displaying it to said user on a base station monitor;
correlating current temperature and atmospheric conditions in said gas kiln to at least one set-point in said recipe for a given elapsed time in said firing process according to said non-volatile instructions input into said base station microcomputer;
generating correlated data including real time time/temperature charts, temperature rise/fall indicators, oxygen content charts, firing progress tables and alerts according to said non-volatile instructions input into said base station microcomputer;

sending an electronic message to a user's mobile device carrier via said local area network, directing said mobile device carrier to send an alert text message to said user's mobile device via said mobile device's carrier system when said alert is generated;

sending real time temperature and atmospheric conditions as well as correlated data to said user's mobile device via a local area network;

displaying said real time temperature and atmospheric conditions and correlated data on said user's mobile device; and accumulating a summary of the firing data in said persistable memory of said base station's microcomputer for later review.

\* \* \* \* \*